(12) United States Patent
Leinders

(10) Patent No.: US 6,482,177 B1
(45) Date of Patent: Nov. 19, 2002

(54) APPARATUS AND METHOD FOR MEASURING THE AMOUNT OF FLUID CONTAINED IN AN IMPLANTABLE MEDICAL DEVICE

(75) Inventor: Robert Leinders, Limbricht (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/394,318

(22) Filed: Sep. 13, 1999

(51) Int. Cl.[7] .............................................. A61M 37/00
(52) U.S. Cl. ..................................................... 604/131
(58) Field of Search .............................. 604/93.01, 118, 604/119, 131, 132, 133, 65, 66, 67, 141–154, 890.1, 891.1, 892.1, 207, 30, 246

(56) References Cited

U.S. PATENT DOCUMENTS

| | | | |
|---|---|---|---|
| 4,619,653 A | * 10/1986 | Fischell | 604/891 |
| 5,328,460 A | 7/1994 | Lord et al. | 604/67 |
| 5,382,236 A | * 1/1995 | Otto et al. | 604/141 |
| 5,443,450 A | 8/1995 | Kratoska et al. | 604/141 |
| 5,643,207 A | 7/1997 | Rise | 604/93 |
| 5,704,922 A | * 1/1998 | Brown | 604/207 |

\* cited by examiner

*Primary Examiner*—Anhtuan T. Nguyen
*Assistant Examiner*—Ann Y. Lam
(74) *Attorney, Agent, or Firm*—Thomas F. Woods; Eric R. Waldkoetter; Tom G. Berry

(57) ABSTRACT

An implantable pump apparatus and method of operating the implantable pump for infusing a fluid into a body as described. An expandable fluid reservoir member includes a first end, a second end, an inlet for receiving the fluid from an outside source and an outlet for dispensing the fluid into the body. A first conductor is operably attached to the first end of the expandable fluid reservoir member. A second conductor is operably attached to the second end of the expandable fluid reservoir member. The level of fluid within the expandable fluid reservoir member is determined by measuring an inductance value at the first conductor that is proportional to the distance between the first conductor and the second conductor.

23 Claims, 2 Drawing Sheets

APPARATUS AND METHOD FOR MEASURING THE AMOUNT OF FLUID CONTAINED IN AN IMPLANTABLE MEDICAL DEVICE

FIELD OF THE INVENTION

The present invention relates to implantable medical devices and associated pump devices for infusing a fluid into a body, and the methods and construction of such devices. Additionally, the present invention concerns the means by which an implantable pump or an implantable medical device measures the amount of fluid contained within the pump.

BACKGROUND OF THE INVENTION

The use of implantable fluid medication dispensers is presently well known in the art. Examples of implantable fluid medication dispensers are contained within U.S. Pat. Nos. 5,328,460, 5,443,450 and 5,643,207. Such dispensers, for example, are used to dispense a specified amount of medication into a patient's body, such as, for example, providing for the delivery of low doses of morphine into a patient's body in an effort to treat cancer pain.

Implantable fluid medication dispensers typically include an internal fluid medication reservoir for receiving, storing and dispensing a supply of a fluid medication. This reservoir is generally included within a housing of some shape or form that may easily be implanted into the body. Other components of the devices include a power source (such as a battery), a mechanism for pumping the fluid medication into the patient's body and a programmable mechanism to assist in dispensing the fluid medication according to a predetermined schedule.

Because these fluid medication dispensers are implanted within a patient's body, which allow them to be portable, they sometimes must be replenished with medication. As a result, the implantable fluid medication dispensers may also include some means to replenish the fluid medication within the reservoir. For reference, please refer to the disclosure of U.S. Pat. No. 5,443,450 to Kratoska, et al. for a discussion of typical reservoir refill assemblies (Column 1, Lines 26–37). Unfortunately, determining the level of mediation contained within the fluid medication dispensers, using a more accurate and less intrusive manner, has, in the past, proved to be problematic. At present, the lack of a fluid medication being dispensed to the patient is generally detected by physiological measures. Such measures, for example, may include symptoms associated with the malady to which the fluid medication is directed to prevent or abate.

There exists, therefore, a significant need for improvement in the measuring abilities of such implantable medication dispensers. Instead of relying upon symptomatic factors, which may cause unwarranted pain to the patient, to determine when an implantable fluid medication device is in need of a replenishment of fluid, it would be desirable to provide a means to determine the amount of fluid remaining in another manner. The present invention fulfills these needs and provides further advantages.

Disclosures relating to implantable medication dispensers include the U.S. Patents listed below in Table 1.

TABLE 1

| Prior Art, United States Patents. | | |
|---|---|---|
| 5,328,460 | July, 1994 | Lord, et al. |
| 5,443,450 | August, 1995 | Kratoska, et al. |
| 5,643,207 | July, 1997 | Rise |

As those of ordinary skill in the art will appreciate readily upon reading the Summary of the Invention, Detailed Description of the Preferred Embodiments and Claims set forth below, at least some of the devices and methods disclosed in the Patents contained within Table 1 may be modified advantageously in accordance with the teachings of the present invention.

SUMMARY OF THE INVENTION

The present invention overcomes at least some of the disadvantages of the prior art by providing a method of and apparatus for measuring the level of a fluid medication within an implantable pump apparatus and fluid medication dispenser, and by providing an improved structure respecting same.

The present invention has certain objects. That is, the present invention provides solutions to at least some of the problems existing in the prior art respecting the measurement of the amount of fluid remaining in an implantable medication dispenser, including the difficulties encountered in prior devices respecting:

(a) providing an accurate measurement of the amount of fluid medication remaining within an implantable pump apparatus;

(b) providing an accurate, reliable diagnosis concerning the amount of fluid medication remaining within the implantable pump apparatus without relying on physiological factors or symptoms of the patient;

(c) providing a safe and nonintrusive means to measure the amount of fluid medication remaining within the implantable pump apparatus without causing harm to the patient;

(d) basing the requirement of additional fluid medication on the detection of physiological factors;

(e) basing the requirement of additional fluid medication on a patient's symptoms; and (f) basing the requirement of additional fluid medication on other inaccurate and potentially unsafe methods.

The present invention provides solutions to at least some of the foregoing problems.

The present invention provides solutions to at least some of the problems associated with known implantable fluid medication dispensers.

Some embodiments of the present invention provide certain advantages including one or more of:

(a) accurately indicating the amount of fluid remaining within an implantable fluid medication dispenser;

(b) safely measuring the amount of fluid remaining within an implantable fluid medication dispenser;

(c) measuring the amount of fluid remaining within an implantable fluid medication dispenser without relying on physiological factors of the patient;

(d) measuring the amount of fluid remaining within an implantable fluid medication dispenser without relying on the symptoms of the patient; and (e) measuring the amount of fluid remaining within an implantable fluid medication dispenser without relying on other inaccurate and potentially unsafe methods.

Some embodiments of the present invention have certain features relating to the measurement of the amount of a fluid medication contained within an implantable fluid medication dispenser, including one or more of:

(a) an expandable reservoir for receiving a specified amount of a fluid medication within an enclosure;

(b) a first conductor operably attached to the first end of the expandable fluid reservoir member; and (c) a second conductor operably attached to the second end of the expandable fluid reservoir member.

BRIEF DESCRIPTION OF THE DRAWINGS

Those foregoing and other advantages and features of the present invention will become apparent upon reading the following Detailed Description and referring to the accompanying Drawings in which like numbers refer to like parts throughout, and in which.

DETAILED DESCRIPTION OF THE PRESENTLY PREFERRED EMBODIMENTS

Figure 1:
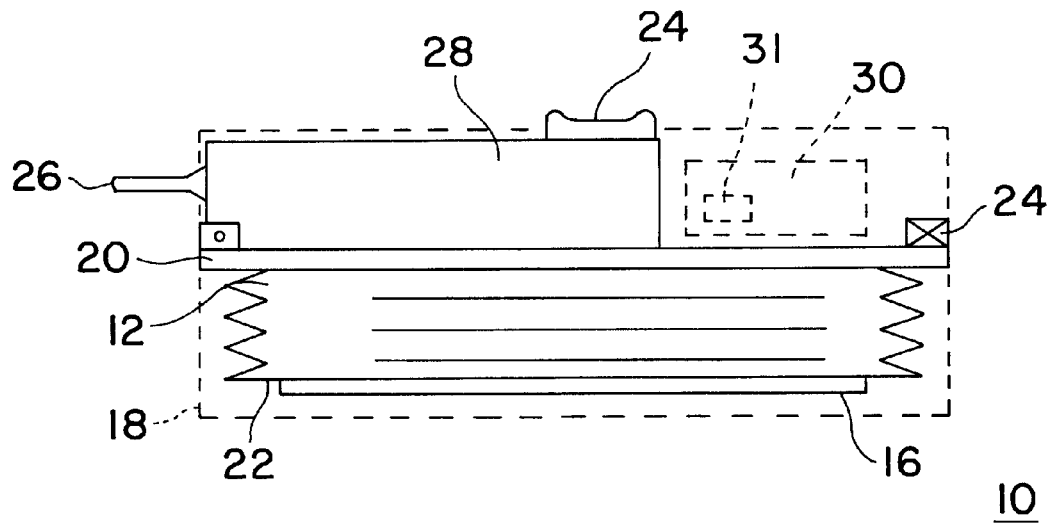
FIG. 1 shows a perspective, cut-away view of the components of one embodiment of an implantable pump apparatus of the present invention.
Figure 2:
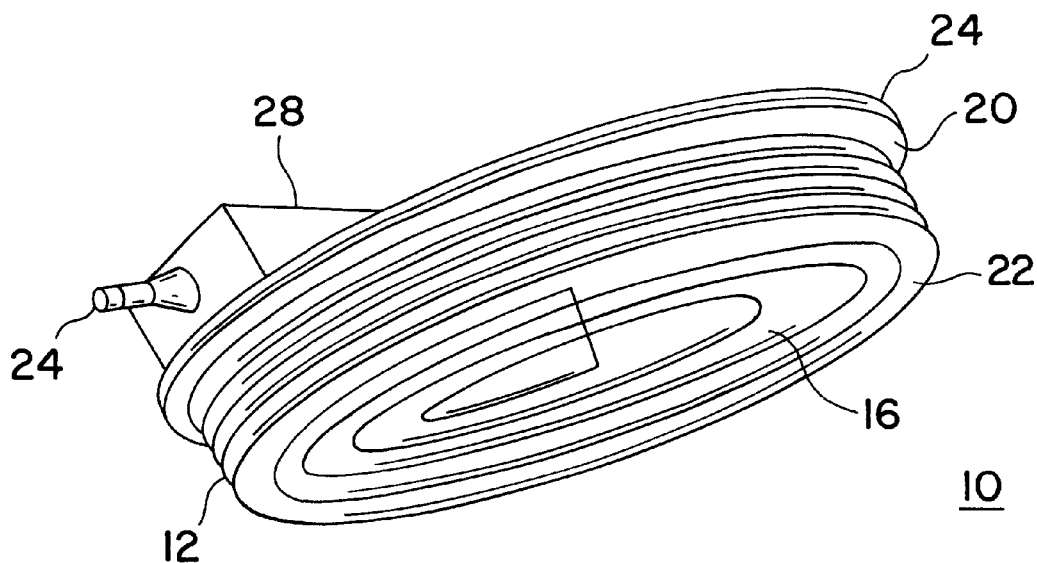
FIG. 2 is a cross-sectional view of the implantable pump apparatus of FIG. 1.

FIG. 1 shows the components of implantable pump apparatus 10 in accordance with one embodiment of the present invention. FIG. 2 shows a cross-sectional view of the implantable pump apparatus 10 of FIG. 1.

The implantable pump apparatus 10 of FIGS. 1 and 2 comprises an expandable fluid reservoir member 12, first conductor 14 and second conductor 16. Shown in phantom, implantable pump apparatus 10 may also include housing member 18.

Expandable fluid reservoir member 12 preferably includes first end 20, second end 22, inlet 24 and outlet 26 (shown in phantom). Expandable fluid reservoir member 12 receives an amount of fluid medication (illustrated by Step 100 in FIG. 3), applied through inlet 24. Additionally, expandable fluid reservoir member 12 dispenses a predetermined amount of fluid medication through outlet 26 (illustrated by Step 200 in FIG. 3). Furthermore, expandable fluid reservoir member 12 may be made of a material that is not absorbed into the body to which implantable pump apparatus 10 is implanted. For example, expandable fluid reservoir member 12 may be formed of niobium, titanium, titanium alloys such as titanium-6A1-4V or titanium-vanadium, platinum, molybdenum, zirconium, tantalum, vanadium, tungsten, iridium, rhodium, rhenium, osmium, ruthenium, palladium, silver and alloys, mixtures and combinations thereof.

Similar to the expandable fluid reservoir member 12, first end 20 may be formed of niobium, titanium, titanium alloys such as titanium-6A1-4V or titanium-vanadium, platinum, molybdenum, zirconium, tantalum, vanadium, tungsten, iridium, rhodium, rhenium, osmium, ruthenium, palladium, silver and alloys, mixtures and combinations thereof. A first side of first end 20 of expandable fluid reservoir member 12 supports bulkhead assembly 28 of implantable pump apparatus 10. Additionally, the first side of first end 20 supports first conductor 14 of implantable pump apparatus 10. The other side of first end 20 (i.e., the second side) provides support for expandable fluid reservoir member 12.

Bulkhead assembly 28 preferably includes electronic measuring device (shown in phantom). Electronic measuring device preferably comprises a conventional electronic circuit of a type well known in the art that determines the inductance value at first conductor 14 of implantable pump apparatus 10, illustrated at Step 300 of FIG. 3.

Figure 3:
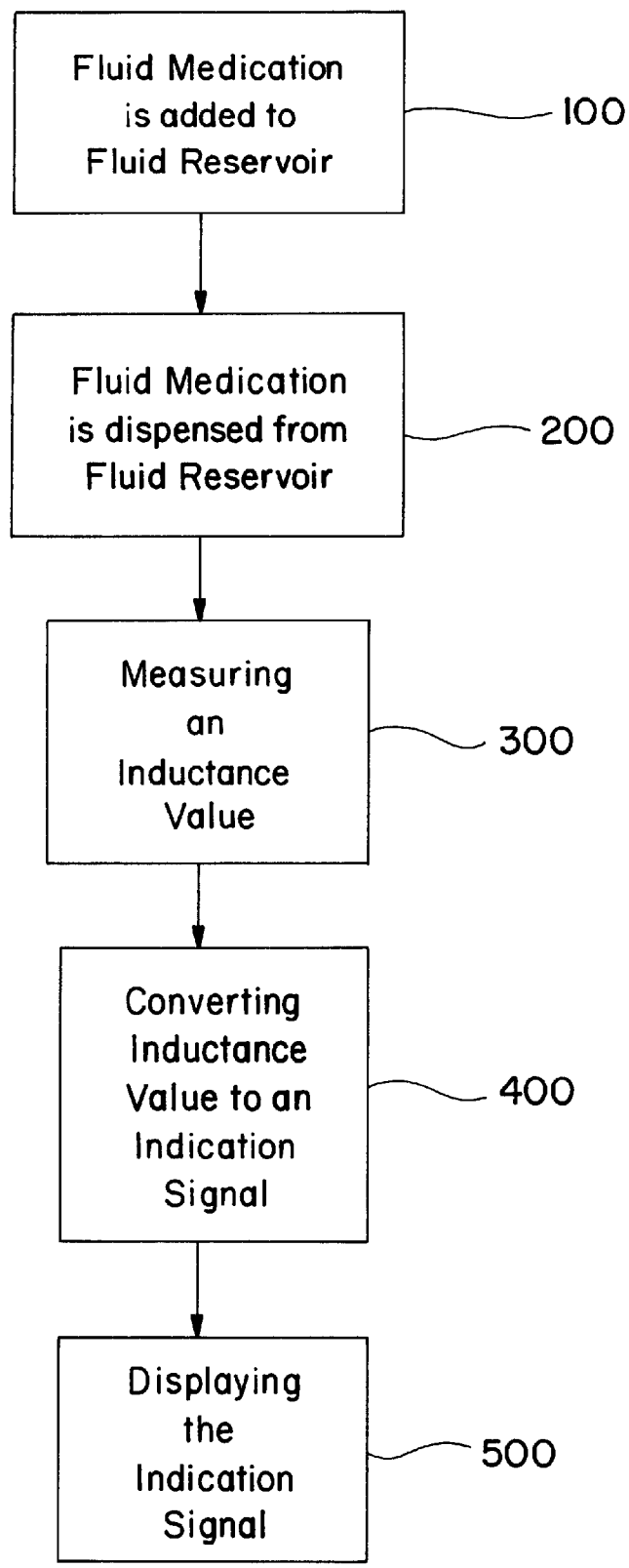
FIG. 3 shows a block diagram of one method of the present invention for measuring a fluid contained within an implantable pump apparatus.

Preferably, after determining the inductance value, the value is converted through conversion device 31 (shown in phantom) into an indication signal corresponding to the level of fluid remaining within expandable fluid reservoir member 12 (illustrated at Step 400 of FIG. 3). The conversion device may comprise any conventional electronic circuit or software program. In other words, the level of fluid will be measured through a translation of the inductance value at first conductor 14 of the implantable pump apparatus 10. The measured inductance value at first conductor 14 is proportional to and correlates with the distance between first conductor 14 and second conductor 16.

Electronic measuring device 30 of bulkhead assembly 28 may include an electronic memory for storing data and signals measured by device 30, and further preferably includes means for communicating with an external device through telemetric, or electromagnetic or RF means well known in the art. A display device preferably forms a portion of such an external device, and permits data gathered or acquired by measurement device 30 to be displayed visually for observation by a human user. The display device receives and displays the indication signal corresponding to the level of fluid in the expandable fluid reservoir member 12 of the implantable pump apparatus 10 (illustrated at Step 500 of FIG. 4). Preferably, the display device is a digital display of the level of fluid in the expandable fluid reservoir member 12. However, the display device may comprise any other similar display means that will accurately portray the level of fluid, such as, for example, an analog display, a Liquid Crystal Display, a Light-Emitting Diode display, and the like Second end 22 of expandable fluid reservoir member 12 of implantable pump apparatus 10 is opposite first end 20. Additionally, second end 22 is in contact with second conductor 16. Also similar to expandable fluid reservoir member 12, second end 22 may be formed of niobium, titanium, titanium alloys such as titanium-6A1-4V or titanium-vanadium, platinum, molybdenum, zirconium, tantalum, vanadium, tungsten, iridium, rhodium, rhenium, osmium, ruthenium, palladium, silver and alloys, mixtures and combinations thereof.

Inlet 24 is preferably disposed on bulkhead assembly 28 of implantable pump apparatus 10. Inlet 24 is preferably configured to receive the fluid that is to be contained within expandable fluid reservoir member 12. Preferably, the fluid may be injected into the expandable fluid reservoir member 12 via inlet 24 by means of a syringe. Alternatively, the fluid may be injected in any other similar manner such as by means of a pump. Therefore, inlet 24 may preferably be any means that allows for the reception of the injector, as described above such as a female receptor adapted to receive a syringe or a pump.

Outlet 26 acts conversely in respect of inlet 24. That is, outlet 26 provides a means through which the fluid contained within expandable fluid reservoir member 12 may be infused into the body at a predetermined rate and/or predetermined intervals. Quantities of fluids dispensed through outlet 26 may also be controlled. It is preferred that outlet 26 be regulated by means of a control device that monitors the amount and timing of fluid permitted to enter the body. Such control devices are well known in the art.

First conductor 14 is disposed on first side of the first end 20 of expandable fluid reservoir member 12. First conductor 14 is preferably electronically connected to electronic measuring device 30 of bulkhead assembly 28. In this way, the electronic characteristics of first conductor 14 (e.g., voltage, resistance, current, etc.) may be transmitted to electronic measuring device 30 of bulkhead assembly 28. Those characteristics may then be employed to calculate such factors as the inductance value of first conductor 14. The inductance value of first conductor 14 may then be extrapolated in an effort to determine the amount of fluid remaining in expandable fluid reservoir member 12. Preferably, first conductor 14 is made of an electrically conductive material such as copper. Alternatively, first conductor 14 may be made of any other suitable electrically conductive material.

Second conductor 16 is disposed on second end 22 of expandable fluid reservoir member 12 of implantable pump apparatus 10. Second conductor 16 may be attached to second end 22 of expandable fluid reservoir member 12 by adhesive means. Alternatively, second conductor 16 may be attached to expandable fluid reservoir member 12 by any other suitable attachment means.

Preferably, second conductor 16 is a short circuit. As a result, second conductor 16 affects the inductance of first conductor 14. Similar to first conductor 14, second conductor 16 is preferably made of an electrically conductive material such as copper. Alternatively, second conductor 16 may be made of any other suitable electrically conductive material.

Although not shown as such in the Figures, housing member 18 encases expandable fluid reservoir member 12. Housing member 18 protects both expandable fluid reservoir member 12 and the body in which expandable fluid reservoir member 12 is implanted. Preferably, housing member 18 is formed of one or more of niobium, titanium, titanium alloys such as titanium-6A1-4V or titanium-vanadium, platinum, molybdenum, zirconium, tantalum, vanadium, tungsten, iridium, rhodium, rhenium, osmium, ruthenium, palladium, silver, and alloys, mixtures and/or combinations thereof.

Although only a few exemplary embodiments of the present invention have been described in detail above, those skilled in the art will appreciate readily that many modifications are possible in the exemplary embodiments without materially departing from the novel teachings and advantages of the present invention. Accordingly, all such modifications are intended to be included within the scope of the present invention as defined in the following claims.

The scope of the present invention is not in any way limited to pumping devices and applications, but extends to other similar medical devices and methods. Additionally, the scope of the present invention is not in any way limited to applications in which a human body is infused with a fluid, but includes similar applications in other mammalians and mammalian organs.

The preceding specific embodiments are illustrative of the practice of the present invention. It is to be understood, therefore, that other expedients known to those skilled in the art or disclosed herein, may be employed without departing from the present invention or the scope of the appended claims.

In the claims, means-plus-function clauses are intended to cover the structures described herein as performing the recited function and not only structural equivalents, but also equivalent structure. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

All patents listed in Table 1, or elsewhere hereinabove, are hereby incorporated by reference into the specification hereof, each in its respective entirety.

I claim:

1. An implantable medical device for infusing a fluid into a body, comprising:

an expandable fluid reservoir comprising a first end, a second end, an inlet for receiving the fluid from an outside source and an outlet for dispensing the fluid into the body, the fluid reservoir being continuously expandable between the first end and the second end from an empty position to a full position, one of the first end being continuously movable with respect to the second end and the second end being movable with respect to the first end as the fluid is either added to or removed from the expandable fluid reservoir;

a first coiled-electrical conductor connected to the first end of the expandable fluid reservoir member;

a second coiled electrical conductor connected to the second end of the expandable fluid reservoir member; and electronic circuit means for measuring the inductance between the first coiled electrical conductor and the second electrical conductor anywhere between the empty position of the fluid reservoir and the full position of the drug reservoir, the electronic circuit inductance measuring means being operably connected to the first and second coiled electrical conductors, the inductance so measured being proportional to a distance separating the first end from the second end.

2. The implantable medical device of claim 1, wherein the electronic circuit inductance measuring means further comprises means for converting the inductance so measured into an indication signal corresponding to the level of fluid in the expandable fluid reservoir.

3. The implantable medical device of claim 2, further comprising a bulkhead assembly member disposed near one of the first end and the second end of the expandable fluid reservoir.

4. The implantable medical device of claim 3, wherein one of the first coiled conductor and the second coiled conductor forms substantially a single coil turn.

5. The implantable medical device of claim 1, wherein the electronic circuit inductance measuring means is operably connected to means for electromagnetically communicating with an external display device.

6. The implantable medical device of claim 5, wherein the display device further comprises means for displaying the indication signal.

7. The implantable medical device of claim 1, further comprising a housing.

8. The implantable medical device of claim 7, wherein the expandable fluid reservoir is disposed within the housing.

9. The implantable medical device of claim 1, the housing is formed of a material selected from the group consisting of niobium, titanium, titanium alloys such as titanium-6A1-4V or titanium-vanadium, platinum, molybdenum, zirconium, tantalum, vanadium, tungsten, iridium, rhodium, rhenium, osmium, ruthenium, palladium, silver, and alloys, mixtures and/or combinations thereof.

10. The implantable medical device of claim 1, wherein the expandable fluid reservoir is formed of a material selected from the group consisting of niobium, titanium, titanium alloys such as titanium-6A1-4V or titanium-vanadium, platinum, molybdenum, zirconium, tantalum, vanadium, tungsten, iridium, rhodium, rhenium, osmium, ruthenium, palladium, silver, and alloys, mixtures and/or combinations thereof.

11. The implantable medical device of claim 1, wherein the first coiled conductor comprises copper.

12. The implantable medical device of claim 1, wherein the second coiled conductor is operably connected to the second end of the expandable fluid reservoir by an adhesive.

13. The implantable medical device of claim 1, wherein the second coiled conductor is short-circuited.

14. The implantable medical device of claim 1, wherein the second coiled conductor comprises copper.

15. A method of measuring an amount of a fluid contained in an expandable drug reservoir disposed within an implantable medical device, the implantable medical device comprising the expandable fluid reservoir, the reservoir comprising a first end, a second end, an inlet for receiving the fluid from an outside source and an outlet for dispensing the fluid into the body, the fluid reservoir being- expandable between the first end and the second end from an empty position to a full position, one of the first end being movable with respect to the second end and the second end being moveable with respect to the first end as the fluid is either added to or removed from the expandable fluid reservoir, a first coiled electrical conductor connected to the first end of the expandable fluid reservoir member, a second coiled electrical conductor connected to the second end of the expandable fluid reservoir member, and electronic circuit means for measuring the inductance between the first coiled electrical conductor and the second electrical conductor anywhere between the empty position of the fluid reservoir and the full position of the drug reservoir, the electronic circuit inductance measuring means being operably connected to the first and second coiled electrical conductors, the inductance so measured being proportional to a distance separating the first end from the second end, the method comprising:

providing the expandable fluid reservoir;

adding the fluid to the expandable fluid reservoir member;

dispensing a portion of the fluid from the expandable fluid reservoir member; and measuring the inductance between the first coiled conductor and the second coiled conductor using the electronic circuit inductance measuring means to determine the amount of fluid in the expandable fluid reservoir member.

16. The method of claim 15, further comprising converting the inductance so measured to an indication signal.

17. The method of claim 16, further comprising providing electromagnetically communicating with an external display device the display device comprising means for displaying the indication signal, and further comprising displaying the indication signal on the display device.

18. The method of claim 15, further comprising providing an hermetically sealed housing adapted for implantation within the body.

19. The method of claim 18, further comprising disposing the expandable fluid reservoir inside the housing.

20. The method of claim 19, further comprising forming the housing from a material selected from the group consisting of niobium, titanium, titanium alloys such as titanium-6A1-4V or titanium-vanadium, platinum, molybdenum, zirconium, tantalum, vanadium, tungsten, iridium, rhodium, rhenium, osmium, ruthenium, palladium, silver, and alloys, mixtures and/or combinations thereof.

21. The method of claim 15, further comprising forming the expandable fluid reservoir from a material selected from the group consisting of niobium, titanium, titanium alloys such as titanium-6A1-4V or titanium-vanadium, platinum, molybdenum, zirconium, tantalum, vanadium, tungsten, iridium, rhodium, rhenium, osmium, ruthenium, palladium, silver, and alloys, mixtures and/or combinations thereof.

22. The method of claim 15, further comprising shorting out the second conductor.

23. The method of claim 15, wherein the expandable fluid reservoir member further comprises an outlet, and further comprising dispensing the fluid from the outlet into the body.

* * * * *

UNITED STATES PATENT AND TRADEMARK OFFICE
CERTIFICATE OF CORRECTION

PATENT NO. : 6,482,177 B1
DATED : November 19, 2002
INVENTOR(S) : Robert Leinders It is certified that error appears in the above-identified patent and that said Letters Patent is hereby corrected as shown below:

Column 6,
Line 30, reads "...position of the drug..."; should read -- ...position of the fluid... --
Line 58, reads "...the housing..."; should read -- ...wherein the housing... --

Column 8,
Line 10, reads "...providing electromagnetically..." should read -- ...proving means for electromagnetically... --

Signed and Sealed this

Fifth Day of April, 2005

JON W. DUDAS
*Director of the United States Patent and Trademark Office*